United States Patent [19]

Gevorgian

[11] Patent Number: 5,484,413
[45] Date of Patent: Jan. 16, 1996

[54] DISPOSABLE MEDICAL SYRINGE WITH SAFETY PROTECTION

[75] Inventor: Abraham Gevorgian, Montebello, Calif.

[73] Assignees: Alexis M. Gevorgian; Artin V. Gevorgian, both of Montebello, Calif.

[21] Appl. No.: 344,937

[22] Filed: Nov. 23, 1994

[51] Int. Cl.⁶ ................................................. A61M 5/00
[52] U.S. Cl. ........................ 604/110; 604/192; 604/220
[58] Field of Search .................................. 604/110, 187, 604/192, 220, 263, 218

[56] References Cited

U.S. PATENT DOCUMENTS

| | | | |
|---|---|---|---|
| 4,233,975 | 11/1980 | Yerman | 604/110 |
| 4,941,879 | 7/1990 | Butler et al. | 604/110 |
| 4,995,869 | 2/1991 | McCarthy | 604/220 X |
| 5,045,063 | 9/1991 | Spielberg | 604/110 |
| 5,259,840 | 11/1993 | Boris | 604/220 X |
| 5,347,078 | 9/1994 | Eckels | 604/192 X |

Primary Examiner—John D. Yasko
Attorney, Agent, or Firm—Gene W. Arant

[57] ABSTRACT

A non-reusable, disposable syringe has a cylindrical barrel with a needle assembly on its forward end, and a needle trap for protecting the needle from contact. The needle trap includes a hollow plastic housing with a rearward end portion adapted to fit over the cylindrical barrel, and a generally cone-shaped forward end portion having a closed forward extremity. A locking member of generally hollow cylindrical shape is secured within the rearward end of the needle trap housing and has forwardly directed flexible, circumferentially spaced, inwardly tapering fingers that taper inwardly more rapidly than the forward end of the housing when the needle trap is placed over the barrel the fingers of the locking member flex outwardly to pass over the needle base and then flex inwardly to assume a locking position behind the needle base.

8 Claims, 3 Drawing Sheets

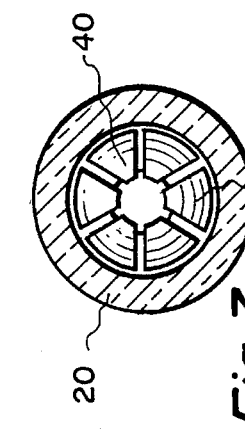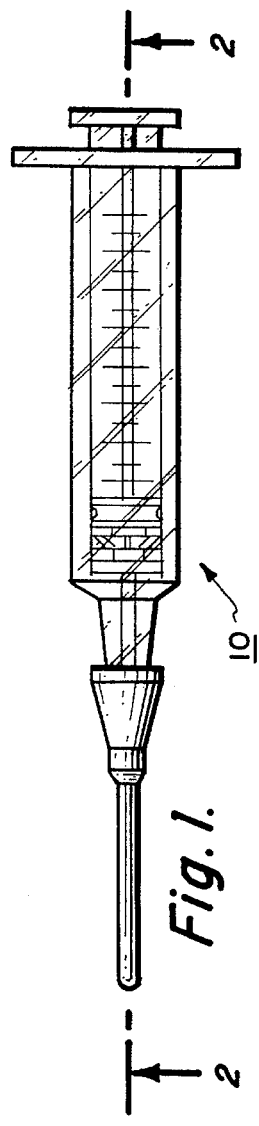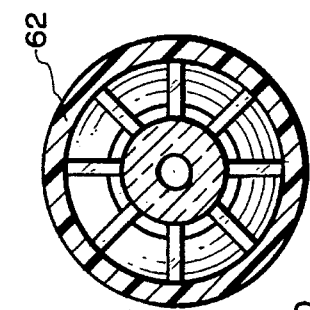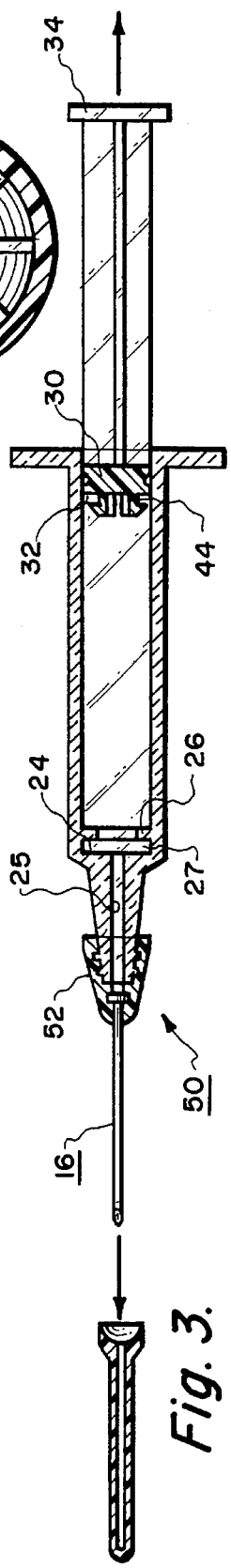

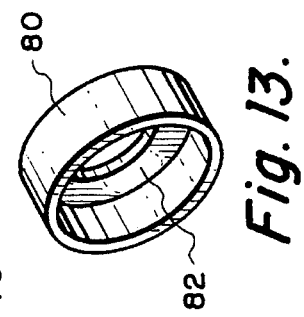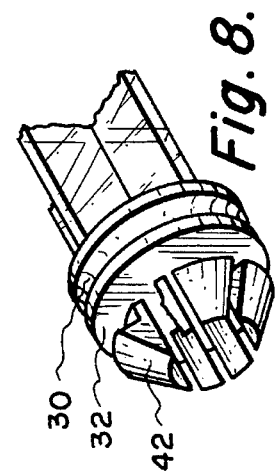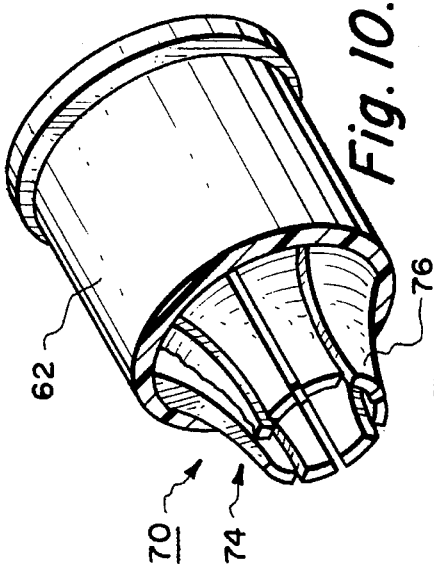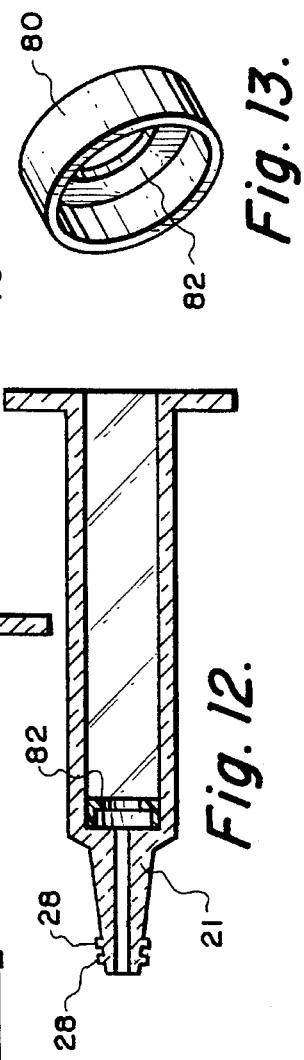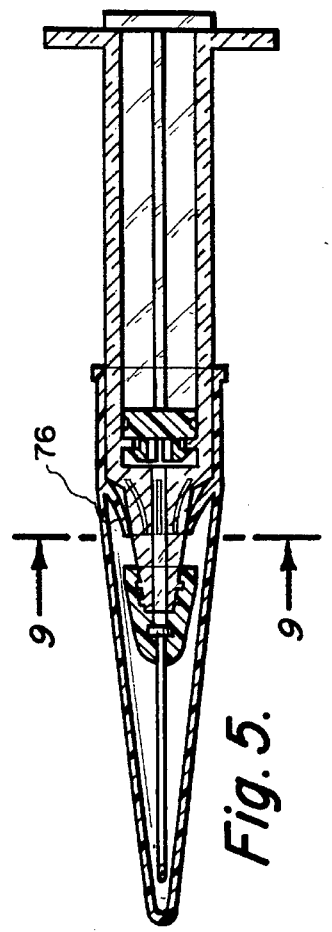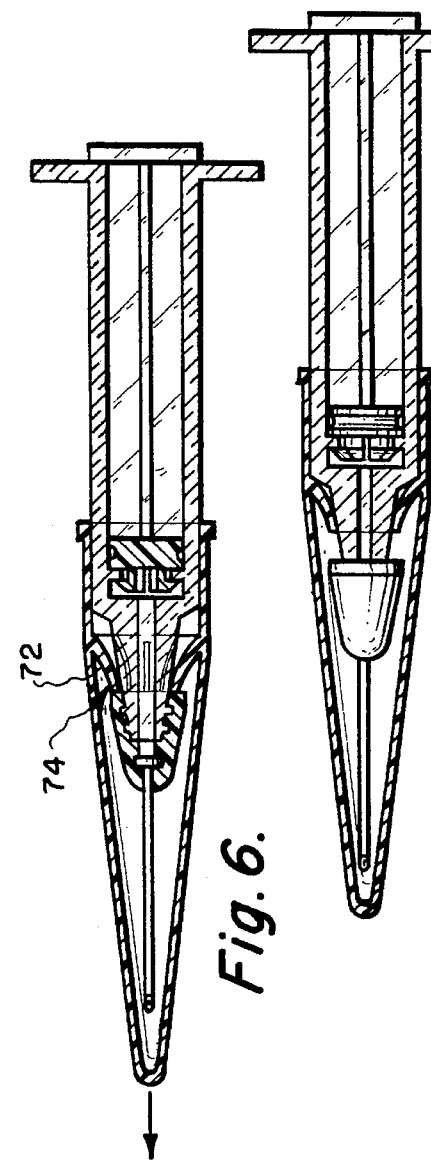

DISPOSABLE MEDICAL SYRINGE WITH SAFETY PROTECTION

BACKGROUND OF THE INVENTION

Disposable hypodermic syringes are widely used throughout the world in hospitals and by the medical profession. Due to the high incidence of infectious diseases in recent years it has become of increasing importance to ensure that the syringe cannot be re-used, and that its needle of cannula is protected against accidental contact.

While many such syringes are inexpensive to manufacture and can therefore be economically disposed of after a single use, it is desirable to provide such a product that is arranged and designed in such a manner that its operation is essentially fool-proof. That is, minimizing the likelihood of human error in the operation and use of the product is extremely important.

SUMMARY OF THE INVENTION

According to one feature of the present invention the barrel and plunger of the syringe are so arranged that after a single discharge of fluid the plunger becomes permanently locked in its forward position in the barrel, preventing any possible re-use.

According to a second and separate feature of the invention a novel needle trap is provided to securely cover the needle after it has been used. The needle trap includes an internal locking member which, when the trap is placed over the needle assembly, securely locks upon the needle base so that the trap cannot be removed, thus making the product safe for subsequent handling by human beings.

DRAWING SUMMARY

FIG. 1 is an exterior view of my new syringe in its fully assembled form and prior to use; FIG. 2 is a longitudinal cross-section view taken on the Line 2—2 of FIG. 1;

FIG. 3 is a longitudinal cross-section view showing my new syringe ready for loading the barrel with a liquid, the needle guard being removed and the plunger being retracted;

FIG. 4 is a longitudinal cross-section view of my new syringe after use, showing the plunger pushed to its forward limit position and locked, and the needle cover about to be put over the needle;

FIG. 5 is a longitudinal cross-section view showing the plunger locked in its forward limit position and the needle cover fully seated in place;

FIG. 6 is a view like FIG. 5 but showing the needle cover jammed after an effort has been made to remove it;

FIG. 7 is a transverse cross-sectional view of the plunger locking mechanism taken on the line 7—7 of FIG. 2;

FIG. 8 is an isometric view of the locking mechanism on the front end of the plunger, partially broken away;

FIG. 9 is a transverse cross-sectional view taken on the line 9—9 of FIG. 5, showing the internal locking structure of the needle cover;

FIG. 10 is an isometric view of the internal locking structure of the needle cover, partially broken away;

FIG. 11 is a view like FIG. 5 but with a different showing of the internal parts;

FIGS. 12 & 13 show an alternate form of the plunger locking mechanism wherein a removable insert ring is placed in the barrel, FIG. 12 being a longitudinal cross-sectional view of the barrel with ring in place and FIG. 13 being an isometric view of the removable ring itself;

DESCRIPTION OF PREFERRED EMBODIMENT

(FIGS. 1–10)

Figure 14:
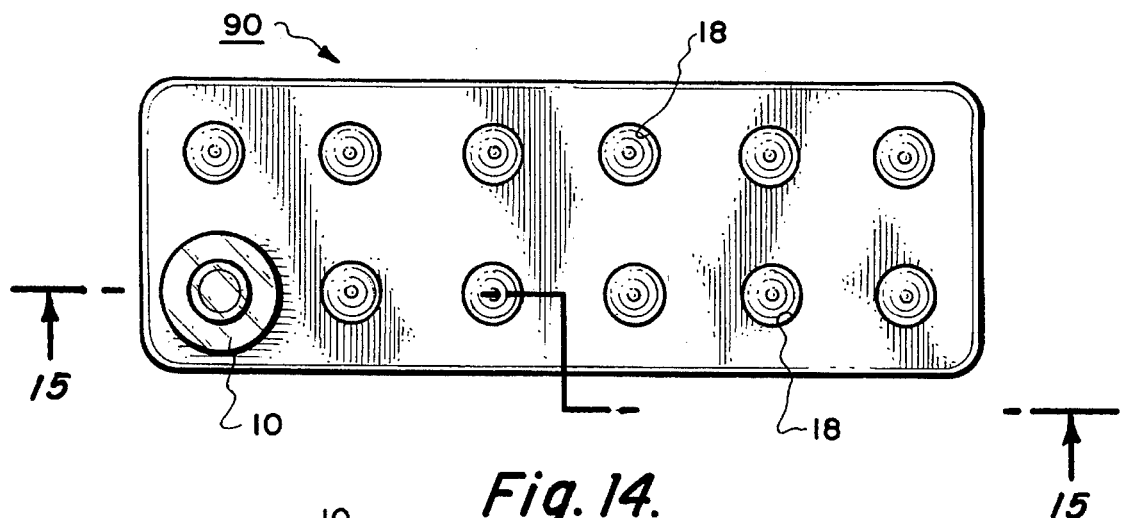
FIG. 14 is a top view of a syringe tray showing a plurality of needles traps permanently built therein, with the syringe in one of the traps.

Reference is now made to FIGS. 1 through 10 of the drawings, which illustrate the presently preferred embodiment of the invention. A hypodermic syringe 10 is adapted to perform the long established medical procedure of an injection underneath the skin of a patient, but is then to be disposed of after a single usage. Principal parts of the syringe 10 are a barrel or tubular housing 12, a plunger 14, and a needle 16. In accordance with the present invention there is also provided a needle trap or safety cover 18. The various parts will be described in more detail.

Barrel 12 has a main cylindrical portion 20 extending through most of its length and a tapered forward end portion 21. Its open rearward end 22 provides a plunger entrance, and also has an outwardly extending rear holding flange 23. At the juncture of the main portion 20 and tapered forward end 21 there is an internal flat circular face 24. An opening 25 in circular face 24 extends longitudinally through the tapered forward end 21 providing a fluid outlet or exit. An annular flange 26 projects from the wall of barrel 12 adjacent to the forward end face 24, but is spaced only a short distance from the face 24 so as to provide a small cylindrical chamber 27 therebetween. External flanges 28 are provided on the exterior surface of the tapered forward end 21 of the barrel, for attaching a needle base, as will be described.

The plunger 14 having the configuration of an elongated rod is disposed in the tubular barrel or housing 12 and movable relative to the housing between a rear position and a forward position. The plunger 14 has on its forward end a pressure plate 30 with a front face 32 for ejecting fluid from the opening 25. A flat circular plate 34 on the rearward end of the plunger 14 provides a handle by which it may be manipulated.

In the conventional operation of the device it may be loaded with a fluid by pushing the plunger 14 to a comparatively forward position, immersing the needle 16 in the fluid, and then retracting the plunger to fill the main barrel part 20 with fluid. In accordance with the present invention the plunger is pushed less than fully forward when loading the syringe with fluid, and all the way forward when the patient is being injected. A means is provided for permanently locking the plunger in its fully forward position so that the device cannot then be re-used.

A resilient locking member 40 is of generally hollow tubular configuration and is fixedly attached to the front face 32 of the pressure plate 30. The locking member 40 has a plurality of forwardly extending and circumferentially spaced flexible fingers 42. Each of the fingers has a radial notch 44 in its outer surface adjacent the pressure plate 30. The length of the fingers forwardly of said notch is no greater than the length of the small cylindrical chamber 27. Pressure plate 30 and locking member 40 are preferably formed of rubber.

A needle assembly 50 includes a needle base 52 fitted over and around the tapered forward end portion 21 of barrel 12 and secured there by the external flanges 28 of the housing or barrel. The needle 16—a hollow tubular instrument with a sharp end point, more scientifically described as a cannula—extends forwardly from the needle base.

It will be noted, particularly in FIG. 8, that the fingers 42 of the locking member 40 are tapered radially inwardly on their forward ends, thus facilitating the inward bending of the fingers in response to engagement with the annular flange 26.

To inject a patient the needle is placed under the patient's skin and the plunger is then pushed forward. When a patient is being injected, during forward movement of the plunger 14 when the locking member 40 starts to pass the annular flange 26, the fingers 42 first contract in a radially inward direction and then expand outwardly until the annular flange 26 is received in all of the slots or notches 44. Thus, any further retraction of the pressure plate 30 is prevented.

The needle trap 18 includes a hollow plastic housing 60 having a cylindrical rearward end portion 62 adapted to fit over the cylindrical barrel part 20. The hollow plastic housing 60 also has a generally cone-shaped forward end portion 64 whose forward extremity 66 is closed. A locking member 70 of generally hollow cylindrical shape is disposed within the hollow plastic housing 60, having a rearward end portion 72 that is firmly secured to the rearward end portion 62 of the housing. Locking member 70 has a forward end portion 74 with flexible, circumferentially spaced, inwardly tapering fingers 76 that taper inwardly more rapidly than the cone-shaped foreward end 64 of the housing 60.

Thus the needle trap is adapted to be placed over the needle assembly and slid over the barrel 12 until the cylindrical rearward end 62 of the plastic housing seats upon the cylindrical barrel part 20. The fingers 72 of the locking member flex outwardly to pass over the needle base 52 and then flexing inwardly to assume a position behind the needle base, thus preventing the needle trap from being removed. As best seen in FIG. 6, an effort to remove the needle trap causes the fingers 76 to jam against the rearward side of the needle base 52.

The locking member 70, 72, 74, 76 is preferably separately formed, and then secured to the cylindrical base 62 by a heat fusion process employing a laser beam to heat the materials at the juncture area.

ALTERNATE FORM (FIGS. 12 & 13)

FIGS. 12 and 13 show an alternate mechanism for locking the

FIGS. 12 and 13 show an alternate mechanism for locking the plunger 14 in its most forward position. The annular flange 26 is omitted from the barrel. A short cylinder 80 has an inturned flange 82 on one end thereof. The cylinder is inserted into the barrel 20 with the flange 82 on its rearward end, and secured there by heat bonding of the plastic materials, or other suitable means. Thus, a short cylindrical space 84 is provided inside the forward end of barrel 20, which may have the same length as space 27 but a somewhat smaller diameter.

Figure 15:
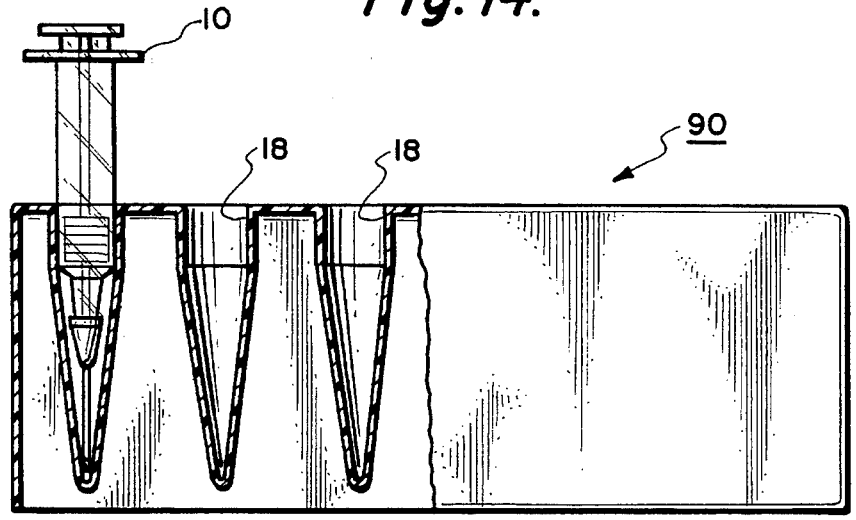
FIG. 15 is a cross-section view of a syringe tray showing the syringe in one of the needle traps.

FIGS. 14 and 15 show how a tray 90 may have a plurality of needle traps 18 permanently built therein. In FIG. 14 one of those needle traps has been filled with a syringe 10.

It will be apparent to those persons skilled in the art that many variations may be adopted, which will accomplish the same general result in the same general way.

The present invention has been described in complete detail in its presently preferred embodiment in order to comply with the disclosure requirements of the patent laws, but it is to be understood that the invention is to be limited only in accordance with the appended claims.

What I claim is:

1. In a non-reusable, disposable syringe having a generally cylindrical barrel with a forward end portion that is tapered to a smaller diameter, and a needle assembly including a needle base fitted over and around said forward end portion of said barrel and a pointed needle extending forwardly of said needle base, a needle trap for protecting the needle from contact, comprising:

a hollow plastic housing having a cylindrical rearward end portion adapted to fit over said cylindrical barrel;

said hollow plastic housing also having a generally cone-shaped forward end portion whose forward extremity is closed;

a locking member of generally hollow cylindrical shape disposed within said hollow plastic housing, having a rearward end portion firmly secured to said rearward end portion of said housing, and a forward end portion with flexible, circumferentially spaced, inwardly tapering fingers that taper inwardly more rapidly than said cone-shaped forward end of said housing;

said needle trap being adapted to be placed over said needle assembly and slid over said barrel until said cylindrical rearward end of said plastic housing seats upon said cylindrical barrel;

said fingers of said locking member flexing outwardly to pass over said needle base and then flexing inwardly to assume a position behind said needle base, thus preventing said needle trap from being removed.

2. The needle trap of claim 1 wherein said fingers of said locking member are adapted to flex outwardly to pass over the needle base and then flex inwardly to assume a position behind the needle base, thus preventing the needle trap from being removed.

3. A non-reusable, disposable syringe comprising:

a barrel having a cylindrical main portion, and a forward end portion tapered to a smaller diameter than said main portion;

a needle assembly including a pointed needle and a needle base, said needle base fitting over and around the tapered forward end portion of said barrel;

a safety cover including a generally cone-shaped housing having an open base end of cylindrical configuration and a closed forward end, and a generally cylindrical locking member disposed within said generally cone-shaped housing;

said locking member of said safety cover further having a cylindrical base fitted within and fixedly secured to said base end of said generally cone-shaped housing, and a tapered forward end forming a plurality of circumferentially spaced flexible fingers, said fingers extending forwardly and also being radially inwardly inclined to a greater degree than said forward end of said generally cone-shaped housing;

said safety cover being adapted to be placed over said needle assembly at the pointed end of said needle and hence slid over said barrel such that said open cylindrical base end of said generally cone-shaped housing fits over said cylindrical main portion of said barrel; and said fingers being also adapted to fit around said forward end portion of said barrel behind said needle base such that said locking fingers then engage said needle base to prevent said cover from being removed from said needle assembly.

4. The non-reusable, disposable syringe of claim 3 wherein said barrel has an open rearward end providing a plunger entrance, and which further includes a plunger inserted into said plunger entrance.

5. The non-reusable, disposable syringe of claim 4 wherein said barrel also has an outwardly extending rear holding flange.

6. The non-reusable, disposable syringe of claim 4 which also includes means for permanently locking said plunger in a fully forward position so that the device cannot then be re-used.

7. A non-reusable disposable syringe as in claim 3, wherein said barrel has an entrance for a plunger at one end and an outlet for fluid at the other end, and which further includes:

a plunger disposed in said housing and movable relative to said barrel between a rear position and a forward position;

said plunger having on its forward end a pressure plate with a front face for ejecting fluid from said barrel; and means for permanently locking said plunger in its forward position so that the device cannot then be re-used, said locking means comprising:

an annular flange projecting from the wall of said barrel adjacent to but spaced a short distance from its forward end so as to provide a small cylindrical chamber;

a resilient locking member of generally hollow tubular configuration fixedly attached to said front face of said pressure plate, said locking member having a plurality of forwardly extending and circumferentially spaced flexible fingers, said fingers having a radial notch in their outer surfaces adjacent said pressure place, and the length of said fingers forwardly of said notch being no greater than the length of said small cylindrical chamber:

so that during forward movement of said plunger when said locking member starts to pass said annular flange, said fingers first contract in a radially inward direction and then expand outwardly until said annular flange is received in said slots, thereby preventing retraction of said pressure plate.

8. The syringe of claim 7 wherein said fingers of said locking member are tapered radially inwardly on their forward ends, thus facilitating the inward bending of said fingers in response to engagement with said annular flange.

* * * * *